(12) United States Patent
Peng (10) Patent No.: US 11,832,912 B2
(45) Date of Patent: Dec. 5, 2023

(54) WIRELESS MAGNETIC ULTRASONIC CAVITATION IN-VIVO THERAPEUTIC ROBOTIC DEVICE

(71) Applicant: Zhijun Peng, Guangdong (CN)

(72) Inventor: Zhijun Peng, Guangdong (CN)

( * ) Notice: Subject to any disclaimer, the term of this patent is extended or adjusted under 35 U.S.C. 154(b) by 317 days.

(21) Appl. No.: 17/380,039

(22) Filed: Jul. 20, 2021

(65) Prior Publication Data

US 2022/0022987 A1 Jan. 27, 2022

(30) Foreign Application Priority Data

Jul. 24, 2020 (CN) .......................... 202010722274.7

(51) Int. Cl.
*A61B 34/00* (2016.01)
*A61B 34/30* (2016.01)
*A61B 17/22* (2006.01)
*A61B 17/00* (2006.01)

(52) U.S. Cl.
CPC ........ *A61B 34/72* (2016.02); *A61B 17/22004* (2013.01); *A61B 34/30* (2016.02); *A61B 2017/00039* (2013.01); *A61B 2017/00221* (2013.01); *A61B 2017/00345* (2013.01); *A61B 2017/00734* (2013.01); *A61B 2017/22007* (2013.01)

(58) Field of Classification Search
CPC ........ A61B 17/22004; A61B 17/22012; A61B 34/30; A61B 34/72; A61B 2017/00039; A61B 2017/00221; A61B 2017/00345; A61B 2017/00411; A61B 2017/00734; A61B 2017/22007; A61B 2017/22008; A61B 2034/303

See application file for complete search history.

(56) References Cited

U.S. PATENT DOCUMENTS

| | | | |
|---|---|---|---|
| 2013/0137921 A1* | 5/2013 | Angot | A61B 1/041 600/109 |
| 2019/0290376 A1* | 9/2019 | Sadan | A61F 2/2412 |

* cited by examiner

*Primary Examiner* — Jocelin C Tanner (57) ABSTRACT

A wireless magnetic ultrasonic cavitation in-vivo therapeutic robotic device, including a micro-robot and an in-vitro control device; the in-vitro control device has an outer housing in which provided with electromagnetic coils and wireless power emitting coils; the micro-robot has a capsule shaped housing in which a super magnetic module is provided; a micro ultrasonic vibrator and a micro wireless power receiving coil electronically connected with each other are provided inside the housing; the wireless power emitting coils emit electromagnetic field to the micro wireless power receiving coil, which receives and then transforms the electromagnetic field to electrical current to supply power to the micro ultrasonic vibrator. The robotic device creates ultrasonic cavitation effect in the blood, causing rapid vibration of blood cells, which enhances cell regeneration power, burn blood lipids, clear blood clots and ensures good condition of blood vessels.

10 Claims, 6 Drawing Sheets

WIRELESS MAGNETIC ULTRASONIC CAVITATION IN-VIVO THERAPEUTIC ROBOTIC DEVICE

BACKGROUND OF THE INVENTION

The present invention relates to the field of micro-robotics, and more specifically relates to a robotic device for unclogging blood vessels.

CN102125453A discloses a robotic device for clearing blood clots in blood vessels. The robotic device is formed by a micro-robot and an external driver. The micro-robot has a bullet shaped housing inside which a separation panel is provided. The separation panel separates an inner cavity of the housing into a clearing chamber and a pump chamber. A section of the housing corresponding to the pump chamber is configured as a flexible corrugated tube. A super-magnetostrictive rod is provided inside the pump chamber. One end of the super-magnetostrictive rod is fixed to the separation panel. Another end of the super-magnetostrictive rod is fixed to a supporting frame. A blood clot collector is provided inside the clearing chamber. One end of the blood clot collector is in communication with the pump chamber through a suction port of the pump chamber. Another end of the blood clot collector is in communication with an external environment external to the micro-robot. The external driver is provided with an annular electromagnetic coil external to the micro-robot. The annular electromagnetic coil is fixed to a movable component. According to the above disclosed invention, by using the super-magnetostrictive rod inside the pump chamber and the flexible corrugated tube of the housing, the super-magnetostrictive rod axially extends and retracts repeatedly under the action force of an alternating or pulsating magnetic field created by the annular electromagnetic coil, and hence causes the flexible corrugated tube to extend and retract axially. Accordingly, the capacity of the pump chamber will be enlarged for repeated number of times so that blood is pumped into the blood clot collector where the blood will be filtered. Also, as the flexible corrugated tube extends axially, a flat end of the bullet shaped housing experiences greater reaction force of the blood compared to a pointed end of the bullet shaped housing, thereby resulting in the micro-robot crawling towards a direction towards the pointed end.

In other words, the above disclosed invention clears blood clots in blood vessels by using the micro-robot that moves inside the blood vessels to collect and filter blood clots in the blood vessels. Also, the blood clots being cleared from the blood vessels are stored inside the blood clot collector of the micro-robot. The applicant of the present invention believes that no significant effect can be resulted in actual implementation of the above disclosed invention. It is known that a micro-robot moving inside human blood vessels has an extremely tiny size in a sense that it is called a "micro" robot. It is therefore expected that the capacity of the blood clot collector of the micro-robot will be even smaller. Accordingly, the volume of blood clots that can be cleared and stored in the micro-robot is negligible. It is required to take out the micro-robot out of the blood vessels for cleaning and restoring and then put it back to the blood vessels again very frequently, and such practice increases the frequency of injuries to body tissues and thus causes greater pain of the patients. In essence, the above disclosed invention is more theoretical than being practical, and it does not achieve good blood clot clearing effect.

BRIEF SUMMARY OF THE INVENTION

In view of above problems and deficiencies in the prior art, the present invention provides a wireless magnetic ultrasonic cavitation in-vivo therapeutic robotic device; the robotic device makes use of the wireless power emitting coils disposed on the in-vitro control device of the robotic device to emit magnetic field to the micro wireless power receiving coil disposed on the micro-robot of the robotic device, and then the micro wireless power receiving coil transforms the magnetic field to electrical current which is then supplied to the micro ultrasonic vibrator for its operation. As the micro ultrasonic vibrator generates high frequency ultrasonic vibration, ultrasonic cavitation effect is created in the blood such that blood cells generate rapid movements. Rapid movements of the blood cells will result in slight frictions between the blood cells, and such slight frictions may alter the size of tissues and cells, relieve swelling, alter membrane permeability, facilitate metabolite exchange, change the functions of cells, and enhance the regeneration power of tissues and cells. Moreover, such slight frictions may clear blood clots in the blood and burn blood lipids. A long term of use may reduce the risk of having blood clots, thereby ensuring good condition of the blood vessels. Also, the present invention can operate inside the blood vessels for a long period of time, it is not necessary to frequently take out the micro-robot to clean and restore and then put it back again, thereby significantly reducing the injuries to muscles and tissues, and thus greatly reducing the pain that may be inflicted on the patient.

The present invention is achieved as follows: A wireless magnetic ultrasonic cavitation in-vivo therapeutic robotic device, comprising a micro-robot and an in-vitro control device; the in-vitro control device comprises an outer housing and electromagnetic coils disposed inside the outer housing; the micro-robot has a capsule shaped housing and a super magnetic module disposed inside the capsule shaped housing; wherein a micro ultrasonic vibrator and a micro wireless power receiving coil are provided inside the capsule shaped housing; the micro wireless power receiving coil and the micro ultrasonic vibrator are electrically connected to provide operating current to the micro ultrasonic vibrator; wireless power emitting coils are provided on the outer housing; the wireless power emitting coils emit electromagnetic field to the micro wireless power receiving coil; the micro wireless power receiving coil receives the electromagnetic field and transforms the electromagnetic field to electrical current to supply power to the micro ultrasonic vibrator so that the micro ultrasonic vibrator generates high frequency ultrasonic vibration.

Further, a micro storage battery is also provided inside the capsule shaped housing; the micro storage battery is electrically connected with the micro wireless power receiving coil; also, the micro storage battery is electrically connected with the micro ultrasonic vibrator.

Further, the capsule shaped housing comprises a front housing, a middle housing and a rear housing; the front housing and the rear housing are both recessed to form a cavity respectively; the middle housing is a hollowed structure having an opened front end and an opened rear end defining a through hole therein.

Further, a vibrator frame and a battery frame are provided in the middle housing; the micro ultrasonic vibrator is mounted onto the vibrator frame; the micro storage battery is mounted onto the battery frame.

The present invention has the following beneficial effects: the robotic device makes use of the wireless power emitting coils disposed on the in-vitro control device to emit magnetic field to the micro wireless power receiving coil disposed on the micro-robot of the robotic device, and then the micro wireless power receiving coil transforms the magnetic field to electrical current which is then supplied to the micro ultrasonic vibrator for its operation. As the micro ultrasonic vibrator generates high frequency ultrasonic vibration, ultrasonic cavitation effect is created in the blood such that blood cells generate rapid movements. Rapid movements of the blood cells will result in slight frictions between the blood cells, and such slight frictions may alter the size of tissues and cells, relieve swelling, alter membrane permeability, facilitate metabolite exchange, change the functions of cells, and enhance the regeneration power of tissues and cells. Moreover, such slight frictions may clear blood clots in the blood and burn blood lipids. A long term of use may reduce the risk of having blood clots, thereby ensuring good condition of the blood vessels. Also, the present invention can operate inside the blood vessels for a long period of time, it is not necessary to frequently take out the micro-robot to clean and restore and then put it back again, thereby significantly reducing the injuries to muscles and tissues, and thus greatly reducing the pain that may be inflicted on the patient. Also, the electromagnetic coils of the in-vitro control device generate a strong magnetic field to drive the super magnetic module, so that the micro-robot can on one hand achieve high frequency ultrasonic vibration in the blood vessels, and on the other hand move and crawl forward. Further, with the help of the high frequency ultrasonic vibration, the micro-robot experiences very small resistance as it moves forward or backward in the blood vessels. Free movements of the micro-robot back and forth in the blood vessels can protect the inner wall of the blood vessels from being impacted or injured. According to the technical solution of the present invention, the present invention can clear blood clots in blood vessels to maintain a good condition of the blood vessels, and may also be used for ultrasonic clearing treatment of phlegm and mucus in the respiratory tract of the lung, or may also be used for ultrasonic cavitation treatment in gastrointestinal organs.

DETAILED DESCRIPTION OF THE INVENTION

Figure 1:
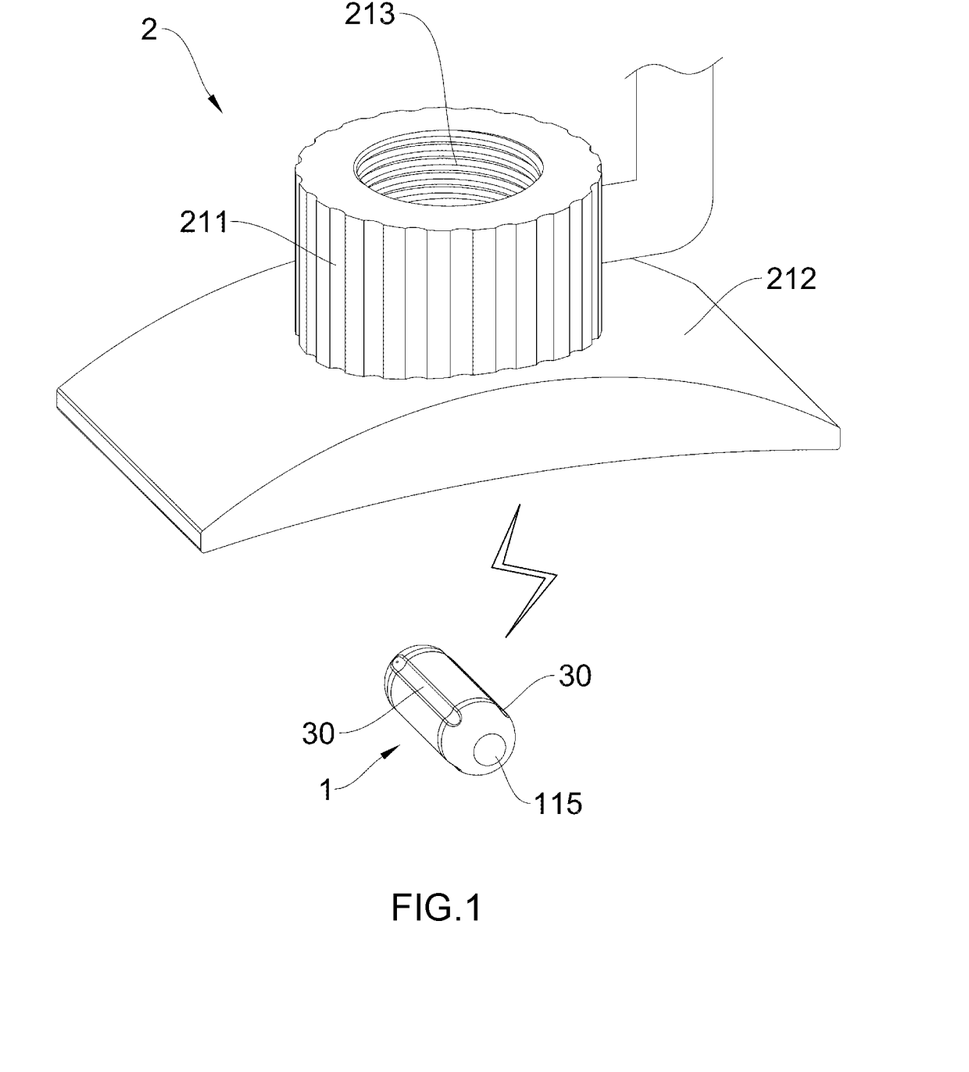
FIG. 1 is a perspective structural view of the present invention.
Figure 2:
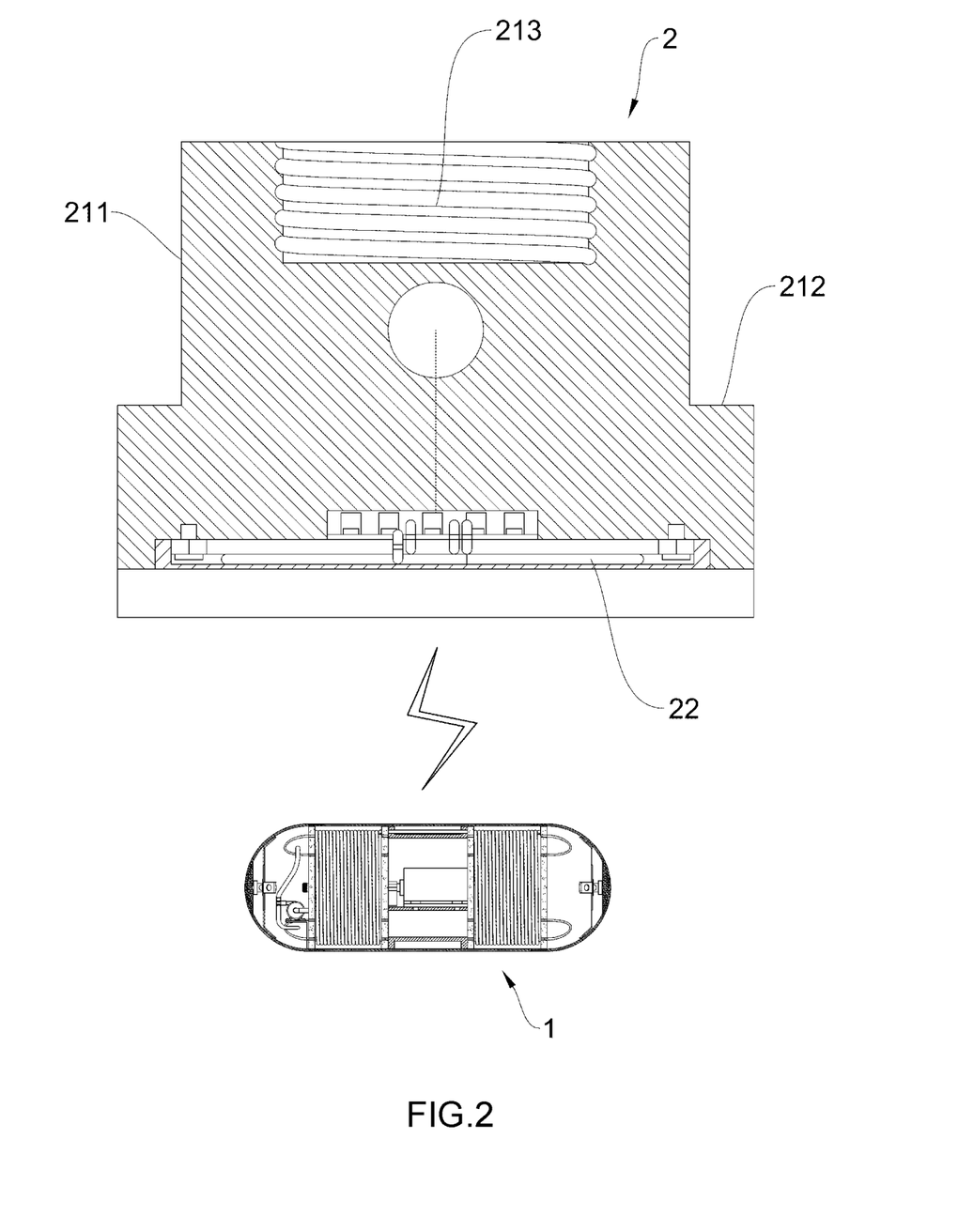
FIG. 2 is a sectional structural view of the present invention.
Figure 3:
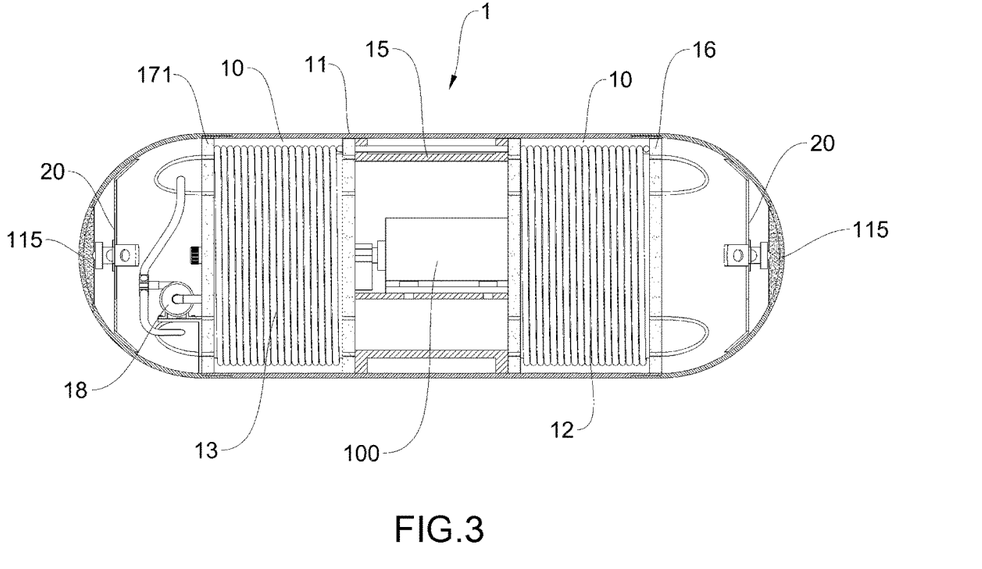
FIG. 3 is a sectional structural view of the micro-robot 1 according to the present invention.
Figure 4:
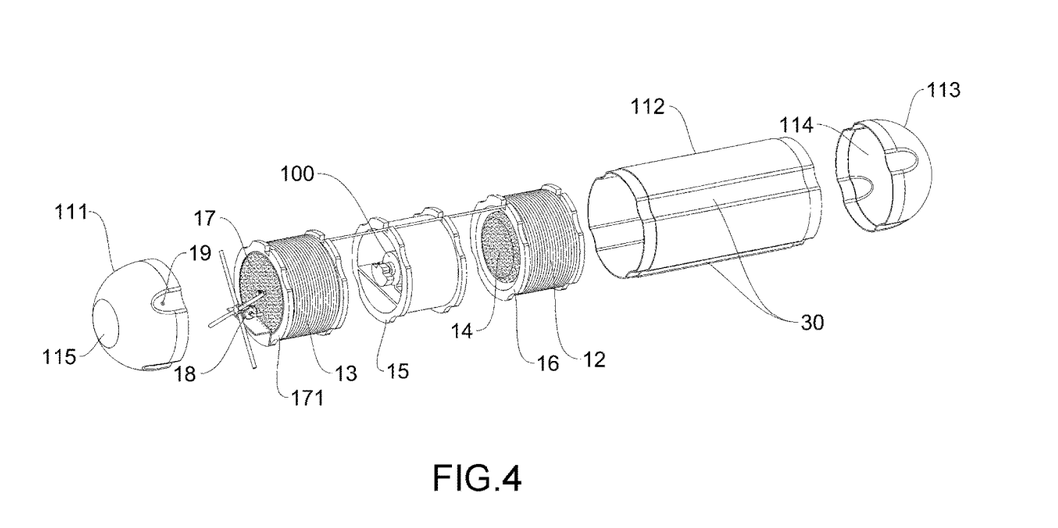
FIG. 4 is an exploded structural view of the micro-robot 1 according to the present invention.
Figure 5:
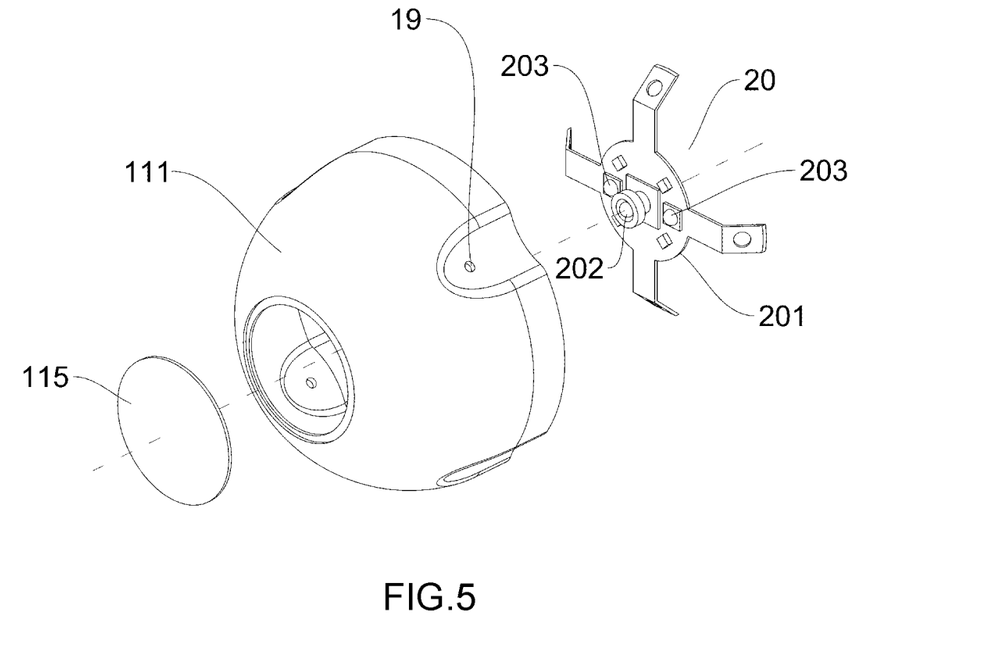
FIG. 5 is an exploded structural view at a location of the micro-robot 1 corresponding to the front housing.

As shown in FIG. 1 and FIG. 2, the present invention discloses a wireless magnetic ultrasonic cavitation in-vivo therapeutic robotic device, comprising a micro-robot 1 and an in-vitro control device 2; the in-vitro control device 2 comprises an outer housing 21 and electromagnetic coils 22 disposed inside the outer housing 21; the micro-robot 1 has a capsule shaped housing 11 and a super magnetic module 12 disposed inside the capsule shaped housing 11. In order to fulfill the objects of the present invention, FIG. 3 and FIG. 4 show a micro ultrasonic vibrator 100 and a micro wireless power receiving coil 13 provided inside the capsule shaped housing 11; the micro wireless power receiving coil 13 and the micro ultrasonic vibrator 100 are electrically connected to provide operating current for the micro ultrasonic vibrator 100; wireless power emitting coils 23 are provided on the outer housing 21; the wireless power emitting coils 23 emit electromagnetic field to the micro wireless power receiving coil 13; the micro wireless power receiving coil 13 receives the electromagnetic field and transform the electromagnetic field to electrical current to supply power to the micro ultrasonic vibrator 100 so that the micro ultrasonic vibrator 100 generates high frequency ultrasonic vibration. The micro ultrasonic vibrator 100 is an ultrasonic motor or ultrasonic transducer.

In order to increase the stability of the present invention during operation so as to be unaffected by fluctuation during wireless power transmission, a micro storage battery 14 is also provided inside the capsule shaped housing 11; the micro storage battery 14 is electrically connected with the micro wireless power receiving coil 13; also, the micro storage battery 14 is electrically connected with the micro ultrasonic vibrator 100. By configuring a micro storage battery 14, the micro storage battery 14 acts as an auxiliary power supply and also stores excessive power so as to prevent fluctuation during wireless power transmission from affecting the operation of the present invention. Accordingly, the present invention can operate stably.

In order that the structures of the present invention are more reasonable and easy to process and achieve, FIG. 4 illustrates the capsule shaped housing 11 comprising a front housing 111, a middle housing 112 and a rear housing 113; the front housing 111 and the rear housing 113 are both recessed to form a cavity 114; the middle housing 112 is a hollowed structure having an opened front end and an opened rear end defining a through hole therein. In order that the micro ultrasonic vibrator 100 and the micro storage battery 14 can be conveniently installed and fixed inside the capsule shaped housing 11, FIG. 3 and FIG. 4 illustrate a vibrator frame 15 and a battery frame 16 provided in the middle housing 112; the micro ultrasonic vibrator 100 is mounted onto the vibrator frame 15; the micro storage battery 14 is mounted onto the battery frame 16.

To enrich the functions of the present invention such that the present invention can achieve auxiliary therapeutic effect by spraying medicines to more seriously clogged locations, FIG. 4 also illustrates a micro medical solution storage can 17 provided inside the middle housing 112; a super micro electrical pump 18 is also provided on a side of the micro medical solution storage can 17. The super micro electrical pump 18 is provided with a solution inlet end connected with the micro medical solution storage can 17; a solution outlet end of the super micro electrical pump 18 is connected with nozzles 19; the nozzles 19 are provided on the capsule shaped housing 11. Likewise, in order that the micro medical solution storage can 17 can be easily mounted onto the capsule shaped housing 11, FIG. 4 illustrates a mounting frame 171 provided around the micro medical solution storage can 17 so that the micro medical solution storage can 17 can be conveniently mounted onto the capsule shaped housing 11.

Further, the in order that the structures of the present invention are more scientific and reasonable, easy to install, and having a more compact size, FIG. 4 illustrates an annular groove 10 provided around each of the micro medical solution storage can 17 and the battery frame 16; the micro wireless power receiving coil 13 winds around the annular groove 10 of the micro medical solution storage can 17; the super magnetic module 12 covers the annular groove 10 of the battery frame 16. The super magnetic module 12 is a permanent magnet made of super magnetic material covering the annular groove 10 of the battery frame 16, or a magnetic field generating electromagnetic coil winding around the annular groove 10 of the battery frame 16.

In order that the user can directly observe operation of the robotic device inside the patient's body, and observe the clogged location inside the patient's body, FIG. 3 and FIG. 4 illustrate a micro camera 20 provided in at least one of the cavity 114 of the front housing 111 and the cavity 114 of the rear housing 113 respectively; each micro camera 20 is formed by a micro circuit board 201, and a micro Bluetooth module, a super micro camera head 202, and LED lighting components 203 disposed on the micro circuit board 201; a transparent cover 115 is provided at an end surface of at least one of the front housing 111 and the rear housing 113 respectively. The micro camera 20 is in communication with an external display, mobile phone, tablet computer or laptop computer via the micro Bluetooth module, so as to transmit and show images to the external display, mobile phone, tablet computer or laptop computer. Also, during actual use, prior art CT scanner or ultrasound apparatus can be used to scan the patient's blood vessels in order to locate the locations where clogging is serious, so that treatment can be specifically targeted to these locations. Further, the in-vitro control device 2 of the present invention can be mounted to an intelligent robotic arm; the intelligent robotic arm can drive the in-vitro control device 2 to control the micro-robot 1 to move such that laboring effect due to manual operation can be reduced.

In order that the robotic device will not pressurize the blood inside the blood vessels as the robotic device moves inside the blood vessels, and hence to further lower the resistance of its movement, FIG. 1 and FIG. 4 illustrate a plurality of guiding grooves 30 arranged on an outer surface of the capsule shaped housing 11 along an axial direction of the capsule shaped housing 11.

Figure 6:
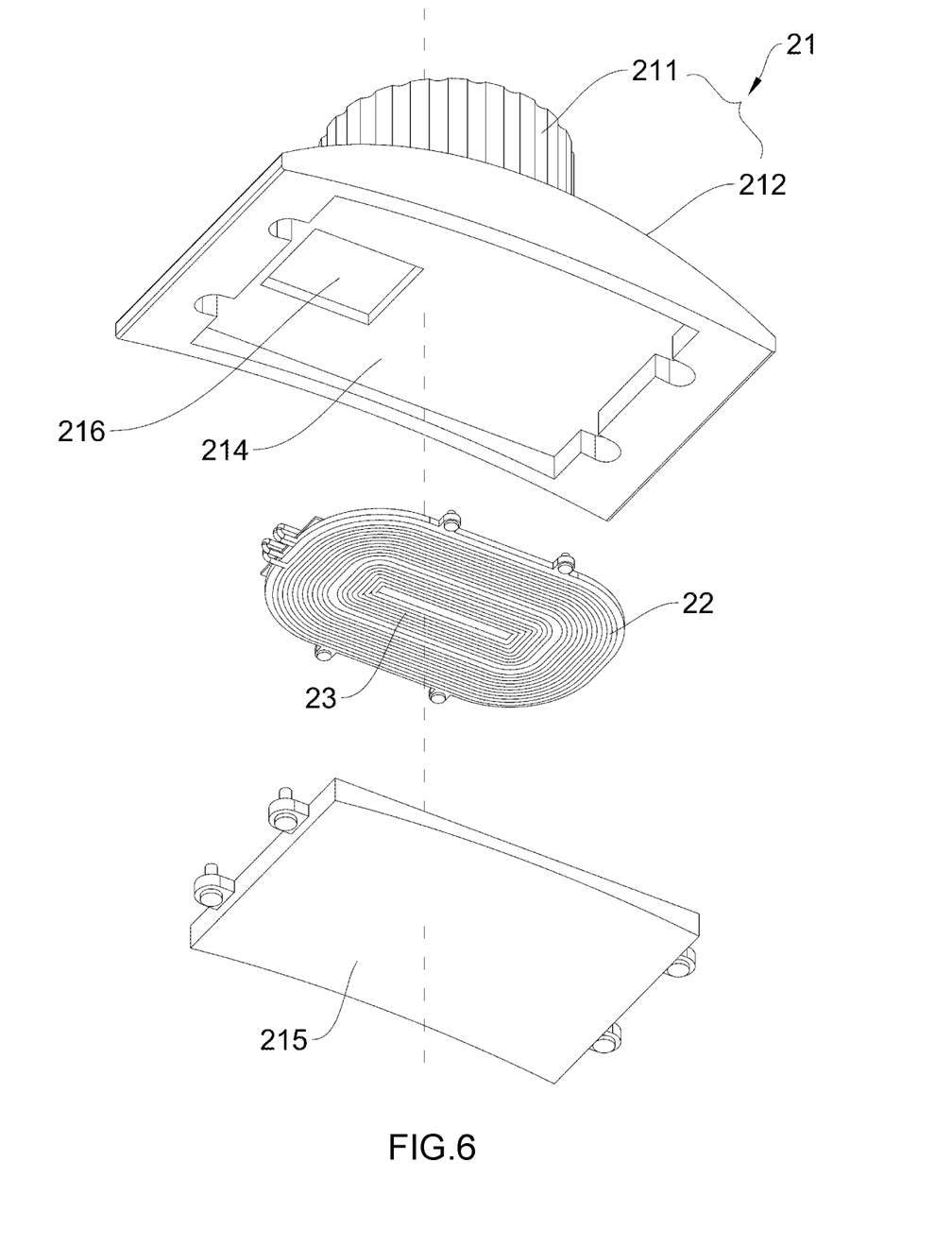
FIG. 6 is an exploded structural view of the in-vitro control device according to the present invention.
Figure 7:
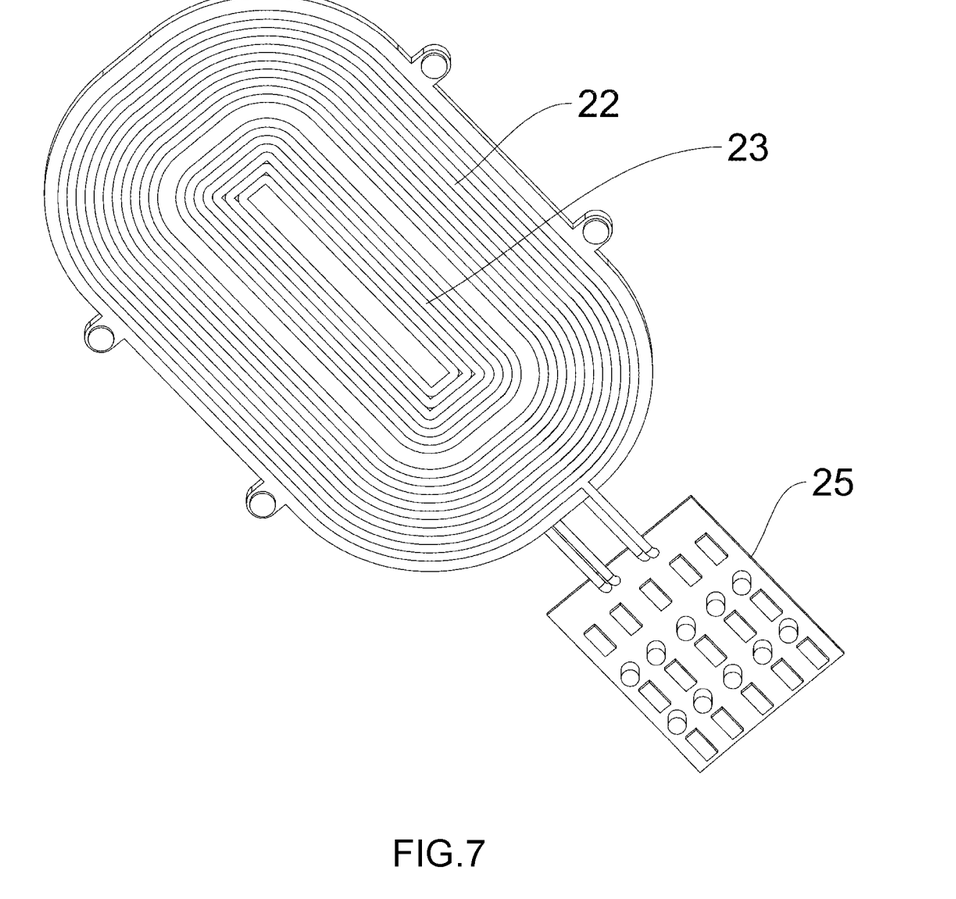
FIG. 7 is a perspective structural view of the electromagnetic coils, the wireless power emitting coils, and the driving circuit board thereof.

In order to further improve the structural configurations of the in-vitro control device 2 of the present invention so that its structures are more reasonable, FIG. 6 and FIG. 7 illustrate the outer housing 21 formed by a grip portion 211 and a base portion 212; a threaded hole 213 is provided at a top side of the grip portion 211; a bottom side of the base portion 212 is provided with a mounting chamber 214 and a chamber cover 215; the electromagnetic coils 22 and the wireless power emitting coils 23 are mounted inside the mounting chamber 214; the chamber cover 215 covers the mounting chamber 214. Also, a circuit board accommodation cavity 216 is also provided inside the mounting chamber 214; a driving circuit board 25 for the electromagnetic coils 22 and the wireless powers emitting coils 23 is mounted inside the circuit board accommodation cavity 216; the threaded hole 213 is adapted to be connected with the intelligent robotic arm.

What is claimed is:

1. A robotic device, comprising a micro-robot and an in-vitro control device; the in-vitro control device comprises an outer housing and electromagnetic coils disposed inside the outer housing; the micro-robot has a capsule shaped housing and a super magnetic module disposed inside the capsule shaped housing; wherein:
   a micro ultrasonic vibrator and a micro wireless power receiving coil are provided inside the capsule shaped housing; the micro wireless power receiving coil and the micro ultrasonic vibrator are electrically connected to provide operating current to the micro ultrasonic vibrator;
   wireless power emitting coils are provided on the outer housing; the wireless power emitting coils emit electromagnetic field to the micro wireless power receiving coil;
   the micro wireless power receiving coil receives the electromagnetic field and transforms the electromagnetic field to electrical current to supply power to the micro ultrasonic vibrator so that the micro ultrasonic vibrator generates high frequency ultrasonic vibration.

2. The robotic device of claim 1, wherein a micro storage battery is also provided inside the capsule shaped housing; the micro storage battery is electrically connected with the micro wireless power receiving coil; also, the micro storage battery is electrically connected with the micro ultrasonic vibrator.

3. The robotic device of claim 2, wherein the capsule shaped housing comprises a front housing, a middle housing and a rear housing; the front housing and the rear housing are both recessed to form a cavity respectively; the middle housing is a hollowed structure having an opened front end and an opened rear end defining a through hole therein.

4. The robotic device of claim 3, wherein a vibrator frame and a battery frame are provided in the middle housing; the micro ultrasonic vibrator is mounted onto the vibrator frame; the micro storage battery is mounted onto the battery frame.

5. The robotic device of claim 3, wherein a micro medical solution storage can is provided inside the middle housing; a super micro electrical pump is also provided on a side of the micro medical solution storage can; the super micro electrical pump is provided with a solution inlet end connected with the micro medical solution storage can; a solution outlet end of the super micro electrical pump is connected with nozzles; the nozzles are provided on the capsule shaped housing.

6. The robotic device of claim 4 or 5, wherein an annular groove is provided around each of the micro medical solution storage can and the battery frame; the micro wireless power receiving coil winds around the annular groove of the micro medical solution storage can; the super magnetic module covers the annular groove of the battery frame.

7. The robotic device of claim 3, wherein a micro camera is provided in at least one of the cavity of the front housing and the cavity of the rear housing respectively; each micro camera is formed by a micro circuit board, and a micro wireless communication module, a super micro camera head, and LED lighting components disposed on the micro circuit board; a transparent cover is provided at an end surface of at least one of the front housing and the rear housing respectively.

8. The robotic device of claim 1, wherein a plurality of guiding grooves are arranged on an outer surface of the capsule shaped housing along an axial direction of the capsule shaped housing.

9. The robotic device of claim 1, wherein the super magnetic module is a permanent magnet made of super magnetic material or a wound magnetic field generating electromagnetic coil.

10. The robotic device of claim 1, wherein the outer housing is formed by a grip portion and a base portion; a threaded hole is provided at a top side of the grip portion; a bottom side of the base portion is provided with a mounting chamber and a chamber cover; the electromagnetic coils and the wireless power emitting coils are mounted inside the mounting chamber; the chamber cover covers the mounting chamber.

\* \* \* \* \*